(12) United States Patent
Taylor (10) Patent No.: US 11,337,699 B2
(45) Date of Patent: May 24, 2022

(54) MAGNESIUM INFUSED SURGICAL BUTTRESS FOR SURGICAL STAPLER

(71) Applicant: Covidien LP, Mansfield, MA (US)

(72) Inventor: Eric J. Taylor, Southington, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/860,123

(22) Filed: Apr. 28, 2020

(65) Prior Publication Data

US 2021/0330326 A1 Oct. 28, 2021

(51) Int. Cl.
*A61B 17/072* (2006.01)

(52) U.S. Cl.
CPC ........... *A61B 17/07292* (2013.01); *A61B 2017/07257* (2013.01); *A61B 2017/07271* (2013.01)

(58) Field of Classification Search
CPC .... A61B 17/07292; A61B 2017/07257; A61B 2017/07271; A61B 17/068–0686; A61B 17/072; A61B 17/07207; A61B 17/115; A61B 2017/00004; A61B 2017/00884; A61L 17/00; A61L 27/047; A61L 27/06
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |

(Continued)

FOREIGN PATENT DOCUMENTS

| | | | |
|---|---|---|---|
| CA | 2282761 A1 | | 9/1998 |
| CN | 109330674 A | * | 2/2019 |

(Continued)

OTHER PUBLICATIONS

SportsCare Physical Therapy, Electrical Stimulation, Sep. 12, 2016 (Year: 2016).*

(Continued)

*Primary Examiner* — Stephen F. Gerrity
*Assistant Examiner* — Linda J Hodge
(74) *Attorney, Agent, or Firm* — Carter, DeLuca & Farrell LLP (57) ABSTRACT

Surgical stapling apparatuses have a surgical buttress attached thereto. The surgical buttress includes an elongate rectangular body having a proximal portion, a distal portion, and opposing lateral sides running along the elongate rectangular body from the proximal portion to the distal portion. Magnesium is on a surface and/or in pores of the surgical buttress.

14 Claims, 4 Drawing Sheets

(56) References Cited

U.S. PATENT DOCUMENTS

| | | |
|---|---|---|
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,443,964 B1 | 9/2002 | Ory et al. |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,021,086 B2 | 4/2006 | Ory et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |

(56) References Cited

U.S. PATENT DOCUMENTS

| | | |
|---|---|---|
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |

(56) References Cited

U.S. PATENT DOCUMENTS

| | | |
|---|---|---|
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 10,682,140 B2 | 6/2020 | Ingmanson et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0081313 A1* | 3/2009 | Aghion .......... A61L 27/58 424/641 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |

(56) References Cited

U.S. PATENT DOCUMENTS

| | | |
|---|---|---|
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0205637 A1* | 7/2014 | Widenhouse .... A61B 17/07292 424/400 |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0305734 A1* | 10/2015 | Melsheimer ....... A61B 17/0218 600/233 |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0303952 A1* | 10/2017 | Nativ ............... A61B 17/07207 |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |

FOREIGN PATENT DOCUMENTS

| | | |
|---|---|---|
| DE | 1602563 U | 3/1950 |
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report issued in corresponding application, EP 21170610.6 dated Oct. 8, 2021 (7 pages).

* cited by examiner

MAGNESIUM INFUSED SURGICAL BUTTRESS FOR SURGICAL STAPLER

TECHNICAL FIELD

The present disclosure relates to medical devices, including surgical devices such as surgical buttresses, for use with wound closure devices.

BACKGROUND

Surgical stapling instruments are employed by surgeons to sequentially or simultaneously apply one or more rows of fasteners, e.g., staples or two-part fasteners, to body tissue for the purpose of joining segments of the body tissue together. Such instruments generally include a pair of jaws or finger-like structures between which the body tissue to be joined is placed. When the stapling instrument is actuated, or "fired", longitudinally moving firing bars contact staple drive members in one of the jaws. The staple drive members push the surgical staples through the body tissue and into an anvil in the opposite jaw, which forms the staples.

In some stapling devices, the staple cartridge jaw member and/or the anvil jaw member include a buttress material that is supported on the anvil jaw member and/or the staple cartridge jaw member to reinforce the staple line applied to tissue. If tissue is to be removed or separated, a knife blade can be provided in the jaws of the device to cut the tissue between the lines of staples and any buttress material applied to the tissue.

Improved surgical repair materials, capable of use as surgical buttresses for sealing and/or reinforcing staple lines against tissue, remain desirable.

SUMMARY

Surgical stapling devices which can be used to repair tissue are provided. In aspects, a surgical stapling device of the disclosure includes an end effector including an anvil jaw member and a staple cartridge jaw member coupled to one another, the anvil jaw member and the staple cartridge jaw member being relatively movable such that the end effector is movable between an open position and a clamped position. A surgical buttress is attached to the staple cartridge jaw member, the surgical buttress having an elongate body connecting a distal portion and a proximal portion, at least a portion of the elongate body including magnesium. The surgical stapling device also includes at least one staple formed of titanium in the staple cartridge jaw member.

In aspects, the magnesium is a coating on the surgical buttress.

In aspects, the surgical buttress is attached to the staple cartridge jaw member by at least one suture.

In some aspects, a second surgical buttress is attached to the anvil jaw member, the second surgical buttress having a second elongate body connecting a distal portion and a proximal portion, at least a portion of the second elongate body including magnesium.

In aspects, the magnesium is a coating on the second surgical buttress.

In aspects, the second surgical buttress is attached to the anvil jaw member by at least one suture.

In some aspects, the surgical buttress is formed of a magnesium film. In other aspects, the surgical buttress is formed of a magnesium foil.

In other aspects, a surgical stapling device of the disclosure includes an end effector including an anvil jaw member and a staple cartridge jaw member coupled to one another, the anvil jaw member and the staple cartridge jaw member being relatively movable such that the end effector is movable between an open position and a clamped position. A first surgical buttress is attached to the staple cartridge jaw member, the surgical buttress having an elongate body connecting a distal portion and a proximal portion, at least a portion of the elongate body including magnesium. A second surgical buttress is attached to the anvil jaw member, the second surgical buttress having a second elongate body connecting a distal portion and a proximal portion, at least a portion of the second elongate body including magnesium. The surgical stapling device includes at least one staple formed of titanium in the staple cartridge jaw member.

In yet other aspects, a surgical stapling device includes an end effector including an anvil jaw member and a staple cartridge jaw member coupled to one another, the anvil jaw member and the staple cartridge jaw member being relatively movable such that the end effector is movable between an open position and a clamped position. A surgical buttress is attached to the staple cartridge jaw member, the surgical buttress having an elongate body connecting a distal portion and a proximal portion, the surgical buttress including a magnesium film or a magnesium foil. The surgical stapling device also includes at least one staple formed of titanium in the staple cartridge jaw member.

In aspects, the surgical stapling device includes a second surgical buttress attached to the anvil jaw member, the second surgical buttress having a second elongate body connecting a distal portion and a proximal portion, the second surgical buttress including a magnesium film or a magnesium foil.

Methods for treating tissue by stapling tissue with the surgical stapling devices of the disclosure are also provided.

BRIEF DESCRIPTION OF THE DRAWINGS

Various aspects of the disclosed surgical stapling device are described herein below with reference to the drawings, wherein.

DETAILED DESCRIPTION

Buttresses are provided for use with tissue fixation devices, such as surgical staples. While the below disclosure discusses in detail the use of these buttresses with staples, it will be appreciated that the disclosed surgical buttresses include a range of buttressing materials and/or film-based materials that may be used to mechanically support tissues, reinforce tissues along staple or suture lines, and decrease the incidence of fluid leakage and/or bleeding of tissues.

The disclosed surgical buttresses may be used with any fixation device utilized to close any wound, defect, and/or opening in tissue. Thus, while surgical buttresses are discussed in conjunction with a surgical stapling apparatus, it is envisioned that other fixation devices, such as tacks, sutures, clips, adhesives, and the like, may be utilized in conjunction with the surgical buttresses of the disclosure to affix the surgical buttresses to tissue.

It should be understood that a variety of surgical stapling apparatuses may be utilized with a surgical buttress. In aspects, linear staplers may be utilized such as, for example, those including EndoGIA™ Reinforced Reload with Tri-Staple Technology™ and other staplers with Tri-Staple™ technology, available through Covidien, (North Haven, Conn.), as well as other anastomosis staplers, such as, for example, EEA™, CEEA™, GIA™, EndoGIA™, and TA™, also available through Covidien. It should also be appreciated that the principles disclosed herein are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus"); laparoscopic staplers (see, e.g., commonly owned U.S. Pat. Nos. 6,330,965 and 6,241,139, each entitled "Surgical Stapling Apparatus"); and transverse anastomosis staplers (see, e.g., commonly owned U.S. Pat. Nos. 5,964,394 and 7,334,717, each entitled "Surgical Fastener Applying Apparatus").

Aspects of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Figure 1:
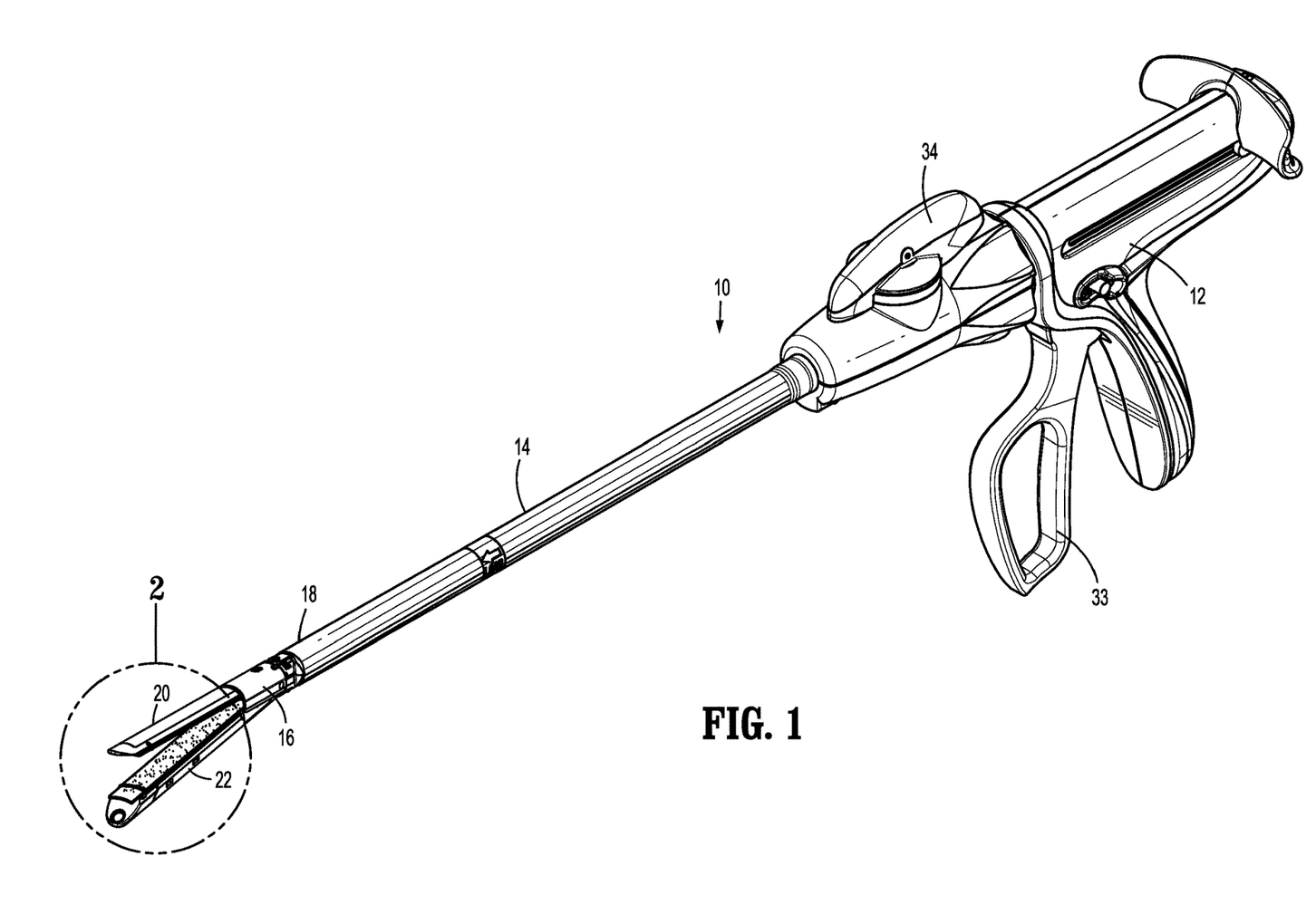
FIG. 1 is a perspective view of a surgical stapling apparatus including a handle housing, an adapter assembly, an end effector, and a buttress attached thereto in accordance with the present disclosure.
Figure 2:
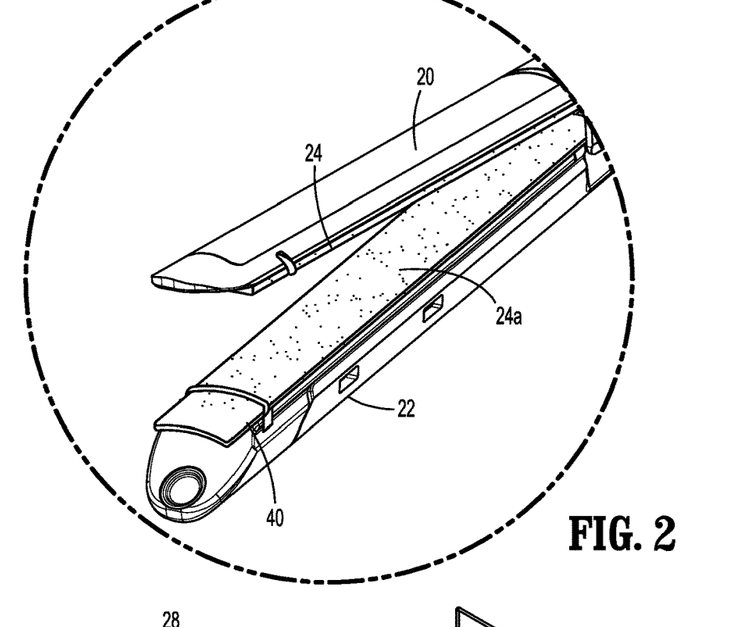
FIG. 2 is an enlarged view of the indicated area of detail shown in FIG. 1.
Figure 3:
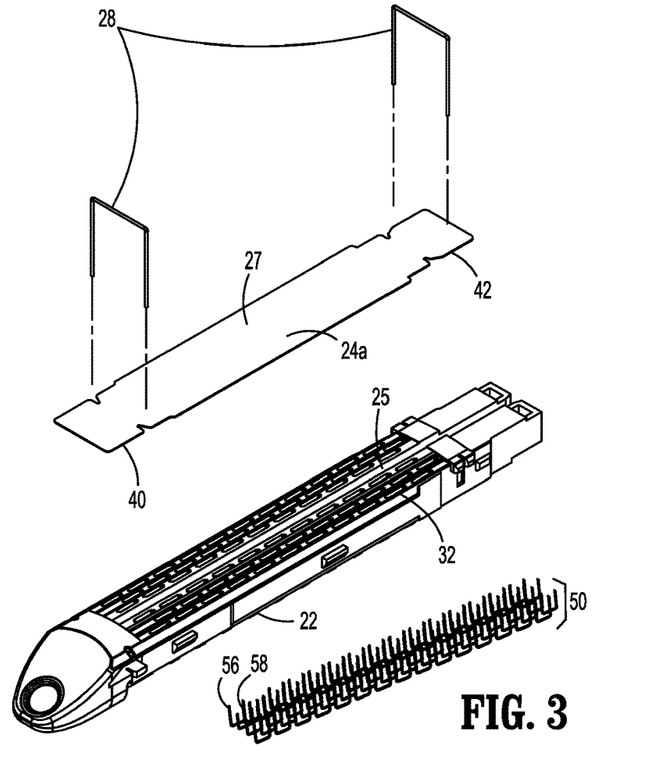
FIG. 3 is a perspective view of a staple cartridge jaw member of the end effector of the surgical stapling apparatus shown in FIG. 1, showing how the buttress may be attached thereto.

FIGS. 1-3 depict an exemplary surgical stapling apparatus or surgical stapler 10 for use in stapling tissue and applying a surgical buttress to tissue. The surgical stapling apparatus 10 generally includes a handle 12 and an adapter assembly including an elongate tubular member 14 extending distally from the handle 12. An end effector 16 is mounted on a distal end 18 of the elongate tubular member 14. The end effector 16 includes an anvil jaw member 20 and a staple cartridge jaw member 22 configured to receive a staple cartridge 32 (FIG. 3). The end effector 16 may be permanently affixed to the elongate tubular member 14 or may be detachable and thus replaceable with a new end effector 16. The anvil jaw member 20 is movably mounted on the distal end 18 of the end effector 16 and is movable between an open position spaced apart from the staple cartridge jaw member 22 to a closed position substantially adjacent the staple cartridge jaw member 22.

The surgical stapling apparatus 10 further includes a trigger 33 (FIG. 1) movably mounted on the handle 12. Actuation of the trigger 33 initially operates to move the anvil jaw member 20 from the open to the closed position relative to the staple cartridge jaw member 22 and subsequently actuates the surgical stapling apparatus 10 to apply lines of staples to tissue. In order to properly orient the end effector 16 relative to the tissue to be stapled, the surgical stapling apparatus 10 is additionally provided with a rotation knob 34 (FIG. 1) mounted on the handle 12. Rotation of the rotation knob 34 relative to the handle 12 rotates the elongate tubular member 14 and the end effector 16 relative to the handle 12 so as to properly orient the end effector 16 relative to the tissue to be stapled.

As depicted in FIGS. 2-3, the anvil jaw member 20 may be provided with a surgical buttress 24, and the staple cartridge jaw member 22 may be provided with a surgical buttress 24a. For ease of reference, the following description will focus on the surgical buttress 24a affixed to the staple cartridge jaw member 22, but it is to be understood that the surgical buttress 24 affixed to the anvil jaw member 20 may be formed of the same materials, having the same configuration and properties as the surgical buttress 24a affixed to the staple cartridge jaw member 22.

Figure 4:
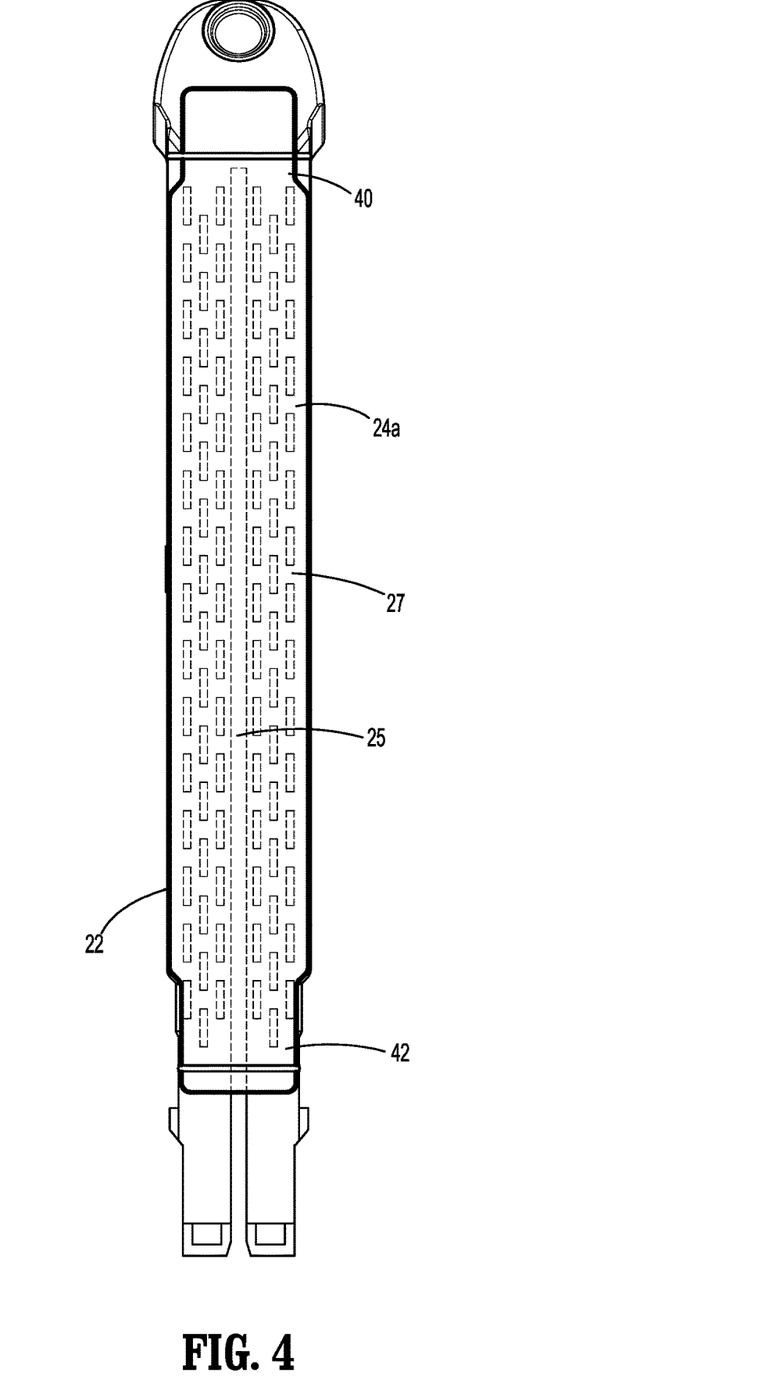
FIG. 4 is a top view of a staple cartridge jaw member of the end effector of the surgical stapling apparatus shown in FIG. 3, showing the buttress attached thereto.

Referring to FIGS. 2-4, the staple cartridge jaw member 22 may be provided with a surgical buttress 24a. The surgical buttress 24a is provided to reinforce and seal staple lines applied to tissue by surgical stapling apparatus 10. The surgical buttress 24a may be configured in any shape, size, or dimension suitable to fit any surgical stapling, fastening, or firing apparatus.

Surgical buttresses may be fabricated from a biocompatible substrate material. Such substrates may be formed of bioabsorbable, non-absorbable, natural and/or synthetic materials.

In aspects, the surgical buttress of the disclosure may be biodegradable, so that the buttress does not have to be retrieved from the body. The term "biodegradable" as used herein is defined to include both bioabsorbable and bioresorbable materials. By biodegradable, it is meant that the surgical buttress decomposes or loses structural integrity under body conditions (e.g., enzymatic degradation or hydrolysis), or is broken down (physically or chemically) under physiologic conditions in the body such that the degradation products are excretable or absorbable by the body.

Non-limiting examples of materials which may be used in forming a surgical buttress of the disclosure include, but are not limited to, poly(lactic acid), poly(glycolic acid), poly (trimethylene carbonate), poly(dioxanone), poly(hydroxybutyrate), poly(phosphazine), polyethylene terephthalate, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly (amino acids), copoly(ether-esters), polyalkylene oxalates, polyamides, poly(iminocarbonates), polyalkylene oxalates, polyoxaesters, polyorthoesters, polyphosphazenes, and copolymers, block copolymers, homopolymers, blends and combinations thereof.

In aspects, natural biological polymers may be used in forming a surgical buttress. Suitable natural biological polymers include, but are not limited to, collagen, gelatin, fibrin, fibrinogen, elastin, keratin, albumin, cellulose, oxidized cellulose, hydroxyethyl cellulose, hydroxypropyl cellulose, carboxyethyl cellulose, carboxymethyl cellulose, chitin, chitosan, and combinations thereof. In addition, natural biological polymers may be combined with any of the other polymeric materials described herein to produce a surgical buttress.

The surgical buttress may also be formed of materials that are porous or non-porous. It should of course be understood that any combination of porous, non-porous, natural, synthetic, bioabsorbable, and/or non-bioabsorbable materials may be used to form the surgical buttress.

In some aspects, the surgical buttress may be formed of porous material(s). Any porous portion of the surgical buttress may have openings or pores over at least a part of a surface thereof. Suitable porous materials include, but are not limited to, fibrous structures (e.g., knitted structures, woven structures, non-woven structures, etc.) and/or foams (e.g., open or closed cell foams).

Where present, the pores may be in sufficient number and size so as to interconnect across the entire thickness of the surgical buttress. Woven fabrics, knitted fabrics, non-woven fabrics and open cell foams are illustrative examples of structures in which the pores can be in sufficient number and size so as to interconnect across the entire thickness of the surgical buttress.

In other aspects, the pores may not interconnect across the entire thickness of the surgical buttress. Closed cell foams or fused non-woven materials are illustrative examples of structures in which the pores may not interconnect across the entire thickness of the surgical buttress. In some aspects, pores may be located on a portion of the surgical buttress, with other portions of the medical device having a non-porous texture. Those skilled in the art may envision a variety of pore distribution patterns and configurations for a porous medical device.

Where the surgical buttress is porous and includes fibrous materials, the surgical buttress may be formed using any suitable method including, but not limited to, knitting, weaving, non-woven techniques (including melt blowing), wet-spinning, electro-spinning, extrusion, co-extrusion, and the like. In aspects, the surgical buttress possesses a three-dimensional structure, such as the textiles described in U.S. Pat. Nos. 7,021,086 and 6,443,964.

Where the substrate used to form the surgical buttress is porous, the surgical buttress may have a pore volume from about 65% to about 85%, in aspects from about 70% to about 80%.

Substrates used to form the surgical buttresses may have a thickness from about 0.05 mm to about 0.5 mm, in aspects from about 0.1 mm to about 0.2 mm.

The surgical buttress includes magnesium. Magnesium may be applied to the surgical buttress, in aspects, by applying a magnesium solution to the substrate used to form the surgical buttress. The solvent of the magnesium solution is then evaporated, so that the magnesium remains on the surgical buttress as a coating on the surgical buttress and/or in the pores of a porous substrate used to form the surgical buttress.

Any suitable solvent may be used to form such the magnesium solution. Exemplary solvents encompass pharmaceutically acceptable solvents including, but not limited to, saline, water, alcohol, acetone, dimethyl sulfoxide, ethyl acetate, N-methylpyrrolidone, combinations thereof, and the like. Methods for forming such solutions are within the purview of those skilled in the art and include, but are not limited to, mixing, blending, sonication, heating, combinations thereof, and the like.

The magnesium solution may be applied to the surgical buttress using any means within the purview of those skilled in the art, including dipping, spraying, solution casting, combinations thereof, and the like.

After application, the solvent may be driven off by methods within the purview of those skilled in the art, including evaporation, heating, the application of a vacuum, combinations thereof, and the like. Solvent evaporation may be facilitated by heat, gas flow, time, reduced pressure, combinations thereof, and the like.

Driving off the solvent leaves the magnesium on the surgical buttress and/or within pores of the surgical buttress.

The resulting surgical buttress may possess magnesium in an amount from about 0.1% by weight to about 50% by weight of the surgical buttress, in aspects from about 1% by weight to about 35% by weight of the surgical buttress, in other aspects from about 5% by weight to about 20% by weight of the surgical buttress.

In other aspects, the surgical buttress itself may be formed of a magnesium film or foil.

As depicted in FIGS. 3-4, the surgical buttress 24a may include an elongate rectangular body portion 27. The rectangular body portion 27 of the surgical buttress 24a has a distal portion 40 and a proximal portion 42. As illustrated in FIG. 3, the surgical buttress 24a may be attached to the staple cartridge jaw member 22 with sutures 28.

Staples 50 used to affix the buttress 24a to tissue are shown in FIG. 3. The staples 50 are formed of a suitable metal, such as titanium.

In aspects, the buttresses 24, 24a described herein may be used in sealing a wound by approximating the edges of wound tissue between the staple cartridge jaw member 22 and the anvil jaw member 20 of the surgical stapling apparatus. Firing of the surgical stapling apparatus 10 forces the staple legs 56, 58 (FIG. 3) of at least one staple 50 to pass through the openings on the staple cartridge jaw member 22, the buttress 24a on the staple cartridge jaw member 22, the tissue, the buttress 24 on the anvil jaw member 20, and the openings on the anvil (not shown) to secure the buttresses 24, 24a to the tissue so that the tissue is sandwiched between the two, thereby securing the adjoining tissue and to seal the tissue.

Upon full actuation of the surgical stapling apparatus 10, a knife (not shown), disposed within knife slot 25 (FIG. 3) cuts tissue captured between the anvil jaw member 20 and the staple cartridge jaw member 22.

Figure 5:
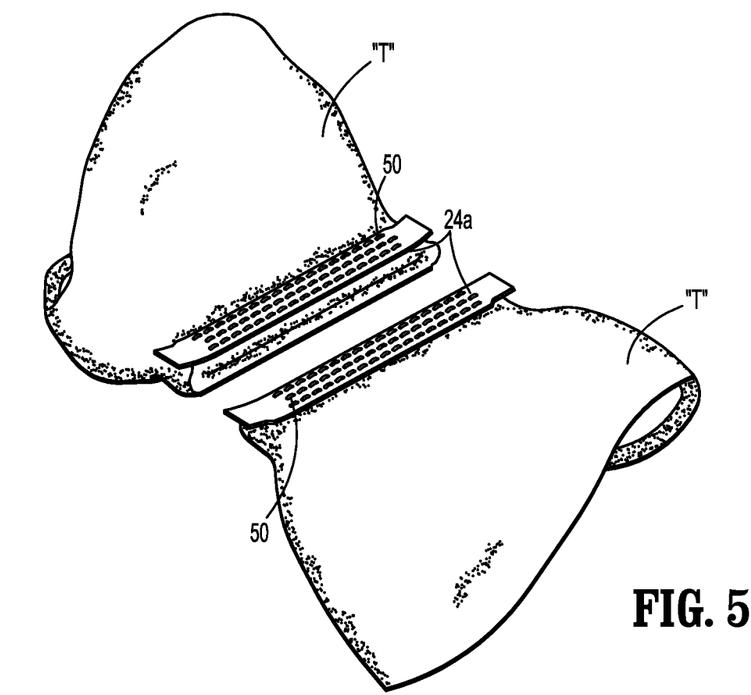
FIG. 5 is a perspective view of a stapled and divided section of tissue after firing of the surgical stapling apparatus of FIG. 1.

The resulting tissue "T", divided and stapled closed with staples 50, is illustrated in FIG. 5. Specifically, the surgical buttress 24a that was associated with the staple cartridge jaw member 22 is secured against tissue "T" by staples 50. Thus, surgical buttress 24a is stapled to tissue "T" thereby sealing and reinforcing the staple lines created by staples 50.

As noted above, a buttress 24 may be applied from the anvil jaw member 20 on the opposite side of the tissue "T" and secured to the tissue "T" by the legs 56 and 58 of the staple 50. In some aspects, the surgical stapling apparatus has the buttress 24a affixed to the staple cartridge jaw member 22, or the buttress 24 affixed to the anvil jaw member 20, but not both.

Upon application to a site of bleeding tissue, the surgical buttress may affect hemostasis of said tissue. As used herein, the term "hemostasis" means the arrest of bleeding.

While the above description is directed to rectangular buttresses, it is to be appreciated that any suitable configuration for a buttress may be utilized in accordance with the present disclosure. For example, buttresses having an elongate rectangular body with head and tail portions at the ends of the buttress may be utilized. Additional suitable buttresses include those disclosed in U.S. patent application Ser. No. 15/639,367, filed Jun. 30, 2017, and U.S. Pat. Nos. 8,157, 151, 8,561,873 and 9,693,772.

The surgical buttress may be used with any fixation device to further assist in sealing tissue. For example, the disclosed surgical buttresses may be used in conjunction with staples, tacks, clips, sutures, adhesives, combinations thereof, and the like.

As noted above, the fixation devices, such as the staples 50, are formed of a metal such as titanium. Electrical stimulation has been suggested to reduce infection, improve cellular immunity, increase perfusion, and accelerate wound healing. In use, the titanium used to form the staples 50 undergoes a galvanic reaction with the magnesium in or on the buttress 24a and/or the buttress 24. This galvanic reaction, a form of electrical stimulation, can accelerate healing of the tissue to which the buttress 24a and/or the buttress 24 is applied.

It will be understood that various modifications may be made to the disclosed surgical stapling devices and surgical buttresses. Therefore, the above description should not be construed as limiting, but merely as exemplifications of aspects of the disclosure. Those skilled in the art will envision other modifications within the scope and spirit of the disclosure. For example, any and all features of one described aspect may be suitably incorporated into another aspect.

What is claimed is:

1. A surgical stapling device, comprising:
   an end effector including an anvil jaw member and a staple cartridge jaw member coupled to one another, the anvil jaw member and the staple cartridge jaw member being relatively movable such that the end effector is movable between an open position and a clamped position;
   a surgical buttress attached to the staple cartridge jaw member, the surgical buttress having an elongate body connecting a distal portion and a proximal portion, at least a portion of the elongate body consists of magnesium; and
   at least one staple formed of titanium in the staple cartridge jaw member.

2. The surgical stapling device of claim 1, wherein the magnesium is a coating on the surgical buttress.

3. The surgical stapling device of claim 1, wherein the surgical buttress is attached to the staple cartridge jaw member by at least one suture.

4. The surgical stapling device of claim 1, wherein a second surgical buttress is attached to the anvil jaw member, the second surgical buttress having a second elongate body connecting a distal portion and a proximal portion, at least a portion of the second elongate body including magnesium.

5. The surgical stapling device of claim 4, wherein the magnesium is a coating on the second surgical buttress.

6. The surgical stapling device of claim 4, wherein the second surgical buttress is attached to the anvil jaw member by at least one suture.

7. The surgical stapling device of claim 1, wherein the surgical buttress is formed of a magnesium film.

8. The surgical stapling device of claim 1, wherein the surgical buttress is formed of a magnesium foil.

9. A method for treating tissue comprising stapling tissue with the surgical stapling device of claim 1.

10. A surgical stapling device, comprising:
    an end effector including an anvil jaw member and a staple cartridge jaw member coupled to one another, the anvil jaw member and the staple cartridge jaw member being relatively movable such that the end effector is movable between an open position and a clamped position;
    a first surgical buttress attached to the staple cartridge jaw member, the first surgical buttress having an elongate body connecting a distal portion and a proximal portion, at least a portion of the elongate body including a coating that consists of magnesium;
    a second surgical buttress attached to the anvil jaw member, the second surgical buttress having a second elongate body connecting a distal portion and a proximal portion, at least a portion of the second elongate body including a coating that consists of magnesium; and
    at least one staple formed of titanium in the staple cartridge jaw member.

11. A method for treating tissue comprising stapling tissue with the surgical stapling device of claim 10.

12. A surgical stapling device, comprising:
    an end effector including an anvil jaw member and a staple cartridge jaw member coupled to one another, the anvil jaw member and the staple cartridge jaw member being relatively movable such that the end effector is movable between an open position and a clamped position;
    a surgical buttress attached to the staple cartridge jaw member, the surgical buttress having an elongate body connecting a distal portion and a proximal portion, the surgical buttress including a film consisting of magnesium or a foil consisting of magnesium; and
    at least one staple formed of titanium in the staple cartridge jaw member.

13. The surgical stapling device of claim 12, wherein a second surgical buttress is attached to the anvil jaw member, the second surgical buttress having a second elongate body connecting a distal portion and a proximal portion, the second surgical buttress including a film consisting of magnesium or a foil consisting of magnesium.

14. A method for treating tissue comprising stapling tissue with the surgical stapling device of claim 12.

* * * * *